United States Patent [19]
Carroll

[11] Patent Number: 5,334,133
[45] Date of Patent: Aug. 2, 1994

[54] IMMOBILIZING CERVICAL COLLAR

[76] Inventor: Terry L. Carroll, 3760 White Rd., Dora, Ala. 35062

[21] Appl. No.: 962,670

[22] Filed: Oct. 19, 1992

[51] Int. Cl.5 .............................. A61F 5/00; A61F 5/37
[52] U.S. Cl. ........................................ 602/18; 128/870
[58] Field of Search ................ 5/635, 636, 637, 81.5; 128/870, 869, 845; 602/18, 19

[56] References Cited

U.S. PATENT DOCUMENTS

| | | | |
|---|---|---|---|
| 2,478,597 | 8/1949 | Scappellino | 5/636 |
| 3,568,890 | 3/1971 | Leachman | 5/636 |
| 3,650,523 | 3/1972 | Darby | 128/870 |
| 3,737,923 | 6/1973 | Prolo | 128/870 |
| 3,892,399 | 7/1975 | Cabansas | 128/870 |
| 3,897,777 | 8/1975 | Morrison | 128/133 |
| 4,182,322 | 1/1980 | Miller | 128/133 |
| 4,252,113 | 2/1981 | Scire | 128/870 |
| 4,297,994 | 11/1981 | Bashaw | 128/133 |
| 4,504,050 | 3/1985 | Osborne | 5/637 |
| 4,655,206 | 4/1987 | Moody | 128/870 |
| 4,886,052 | 12/1989 | Calabrese | 602/18 |
| 4,928,711 | 5/1990 | Williams | 128/869 |
| 5,027,833 | 7/1991 | Calkin | 128/870 |
| 5,038,759 | 8/1991 | Morgenstern | 602/18 |

Primary Examiner—Michael A. Brown
Attorney, Agent, or Firm—Veal & Associates

[57] ABSTRACT

A cervical collar for immobilizing the head and neck of a patient to a backboard. A base attached to posterior portion of said collar rests within a recess defined by a frame mounted upon said backboard. A sliding member secures said base within said recess of said frame and is locked into place by a pin and groove latch.

17 Claims, 6 Drawing Sheets

IMMOBILIZING CERVICAL COLLAR

FIELD OF THE INVENTION

The present invention relates to a cervical collar for immobilizing the head and neck of an injured person. More particularly the invention relates to a cervical collar that can be detachably secured to a patient backboard or similar support means. In greater particularity, the invention relates to a cervical collar with a base which can be secured to a locking frame mounted on a patient backboard or similar support device.

BACKGROUND OF THE INVENTION

When moving an accident victim it is imperative that the head and cervical portion of the victim be immobilized. Immobilization prevents further possible damage to various portions of the victim's spine during treatment and transportation. Over the years, a number of immobilizing devices have been used in emergency and medical situations.

Cervical collars are often used to prevent an accident victim or patient from turning his or her head and neck. These collars normally comprise two halves that encircle the wearer's neck providing rigid support for the cervical vertebrae.

Often, a cervical collar alone is not sufficient to immobilize the head and neck of a patient. It may be necessary to immobilize the victim's head and neck to a backboard or similar support means. Historically, this type of immobilization was accomplished by placing sandbags on either side of the victim's head and taping the head to the backboard. More recently developed devices use foam cushions or pillows to immobilize the patient's head while straps hold the pillows in place as shown in U.S. Pat. No. 3,897,777 (issued to R. Morrison on Aug. 5, 1975).

Another example of a device for restraining the head and neck is disclosed in U.S. Pat. No. 4,297,994 (issued to R. W. Bashaw on Nov. 3, 1981). This device includes a headband with a pair of cushions which attaches to a support board by Velcro-like strips.

Still other devices use a plurality of adjustable straps which are permanently attached to the support board for immobilizing the patient's head and neck along with the rest of the patient's body.

In U.S. Pat. No. 4,928,711, G. R. Williams provides a fold-up head support device that can be attached to a support means prior to its use.

All of the devices mentioned above and those similar in design have significant drawbacks when used in actual emergency situations. Patients in emergency situations often suffer a number of serious injuries requiring immediate medical attention. The time it takes to prepare and transport a patient can be the difference between life and death. In some instances, the faster a patient can get to a fully equipped trauma center the greater that patient's chances of survival. Increased use of quick response medical services such as helicopters, bolsters the emphasis on fast preparation and transport of patients.

Immobilization devices which require numerous straps and buckles can hinder emergency assistance process by wasting valuable time. In a similar fashion, complicated devices use valuable time to set up.

Many of the immobilization devices used in conjunction with backboards are composed of numerous parts and pieces. These parts and pieces are subject to loss and misplacement when not in use. The frantic nature and pace of an emergency scene can also lead to misplacement of vital parts and pieces. Some immobilization devices are rendered unusable when a small part or piece is missing.

There is a current need for a simple device for immobilizing an injured person's head and neck to a support board or similar device.

A further disadvantage found in current immobilization devices is that they easily absorb bodily fluids such as blood. The foam inside many cervical collars is porous in nature and readily absorbs bodily fluids. Support pillows in some immobilization devices invite similar absorbtion problems.

The fluids absorbed into these devices pose a cleaning problem before these devices can be reused. Major health concerns arise from the possibility of subsequent patients coming in contact with the absorbed bodily fluid. In particular, the rapid spread of the infectious disease AIDS presents a significant contamination hazard. Devices may become so inundated with fluid that they must be discarded before their useful lives have ended. There is a need for an immobilization device having easy-to-clean surfaces.

In generally reviewing the immobilizing devices found in the industry, a need can be seen for a head and neck immobilizing device that can be easily attached to a backboard or similar support means. Such an immobilizing device must be simple in design and quickly deployed. Additionally such a device must be easily cleaned to prevent the possibility of contaminating subsequent patients.

SUMMARY OF THE INVENTION

It is an object of this invention to provide an improved head and neck immobilizing device rectifying some shortcomings of previous devices.

It is also an object of this invention to provide an immobilizing device which is quickly and easily detachable to a backboard or similar support board.

It is a further object of this invention to provide an immobilizing device which is easily cleaned for reuse.

It is yet another object of this invention to provide simple immobilizing device with few parts and pieces for attaching the immobilizing device to a backboard or similar support board.

These and other objects and advantages of my invention are accomplished through the use of a quick locking cervical collar. A two-piece cervical collar encircles an injured person's neck to prevent further injury to spine, etc. The lower cervical collar piece has an attached base with an opening or openings extending through the width of the base. A locking frame permanently mounted on a backboard defines a recessed seat for accepting the base and attached cervical collar. The base can be secured within the recess by a plate member slidably through sides of locking frame and openings of the base.

The slidable member can be locked into place on the mounted frame to prevent disengagement. Further the plate may have flanges or tabs to prevent complete disengagement from the mounted frame.

BRIEF DESCRIPTION OF THE DRAWINGS

Apparatus embodying features of my invention are depicted in the accompanying drawings which form a portion of this disclosure and wherein.

DESCRIPTION OF THE PREFERRED EMBODIMENT

Figure 1:
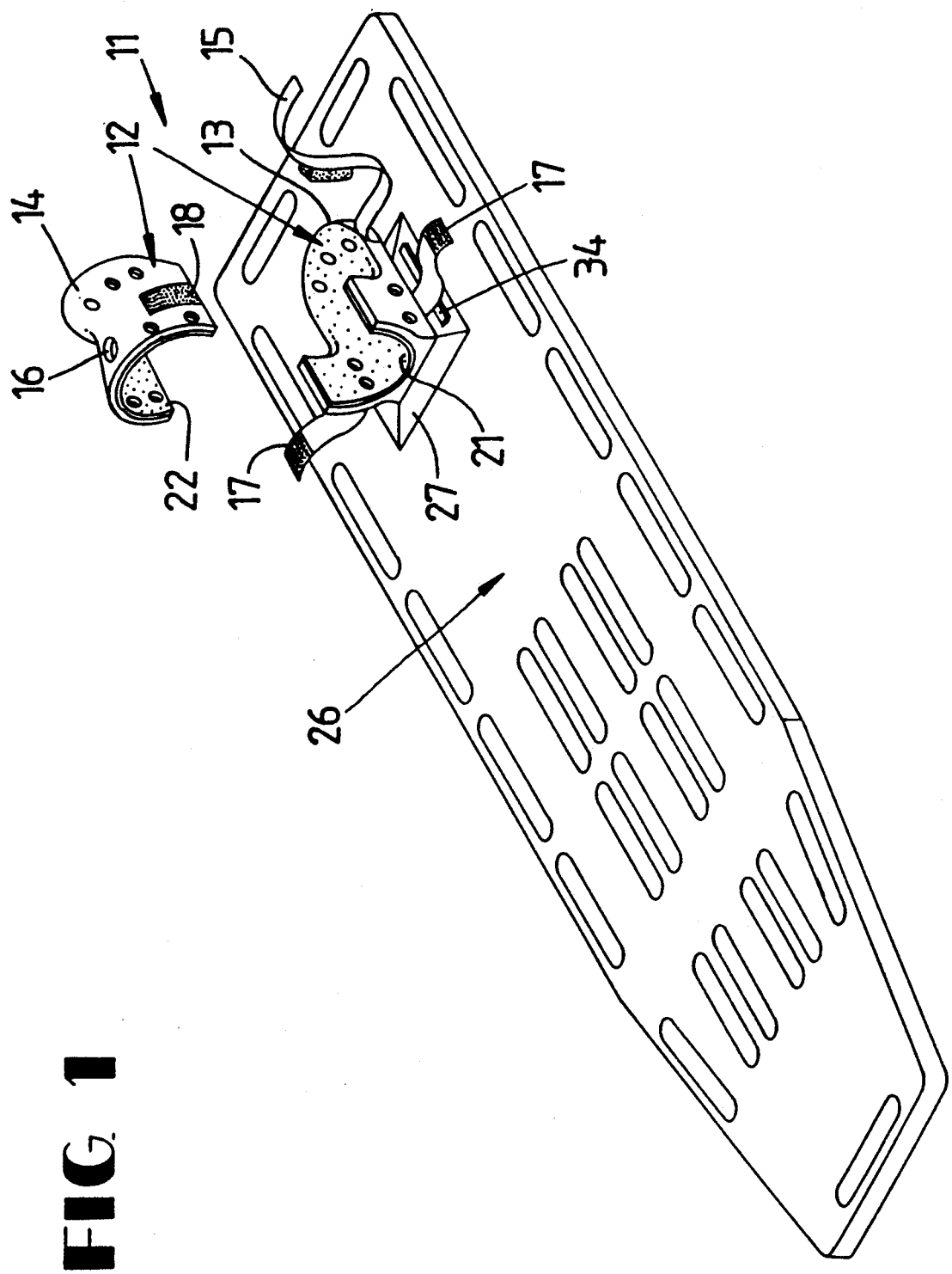
FIG. 1 is a perspective view of the improved immobilizing device.

Referring to the drawings for a clearer understanding of the invention FIGS. 1–4 show a preferred embodiment of head and neck immobilizing device 11 which can be attached to a patient backboard.

In FIG. 1 a cervical collar 12 includes a posterior member 13 for engagement behind the head and cervical region of a patient. An anterior member 14 supports the mandibular region of a patient and is detachably secured to posterior member 13 to encircle a patient's neck. Members 13 and 14 may be formed from hard plastics such as polyvinyl chloride or polyethylene. The anterior member 14 has an aperture 16 extending therethrough to allow access to a patient's trachea.

Posterior member 13 has strips of Velcro type hook material 17 attached to either side at an area near the patient's neck. Patches of Velcro type loop material 18 are secured to outside surface on either side of anterior member 14. When the anterior 14 and posterior 13 member are in place around patient's neck, the strips 17 interlock with loop material 18 to secure the cervical collar 12 in variable position. A padded head strap 15 holds patient's head to posterior member 13.

Liner pads 21 and 22 are formed from a unicellular PVC foam and then coated with vinyl. Liner pad 21 is formed to fit within posterior member 13 and is held in place by Velcro type hook strips and loop patches not shown. In similar fashion, a liner pad 22 fits into anterior member 14 as shown in FIG. 1. These replaceable liner pads 21 and 22 facilitate easy cleaning as absorbtion of bodily fluids, especially blood, is reduced by the vinyl coating. When the cleaning of pads 21 and 22 is no longer an option, the pads 21 and 22 may be replaced in lieu of disposing of an entire collar 12.

Figure 2:
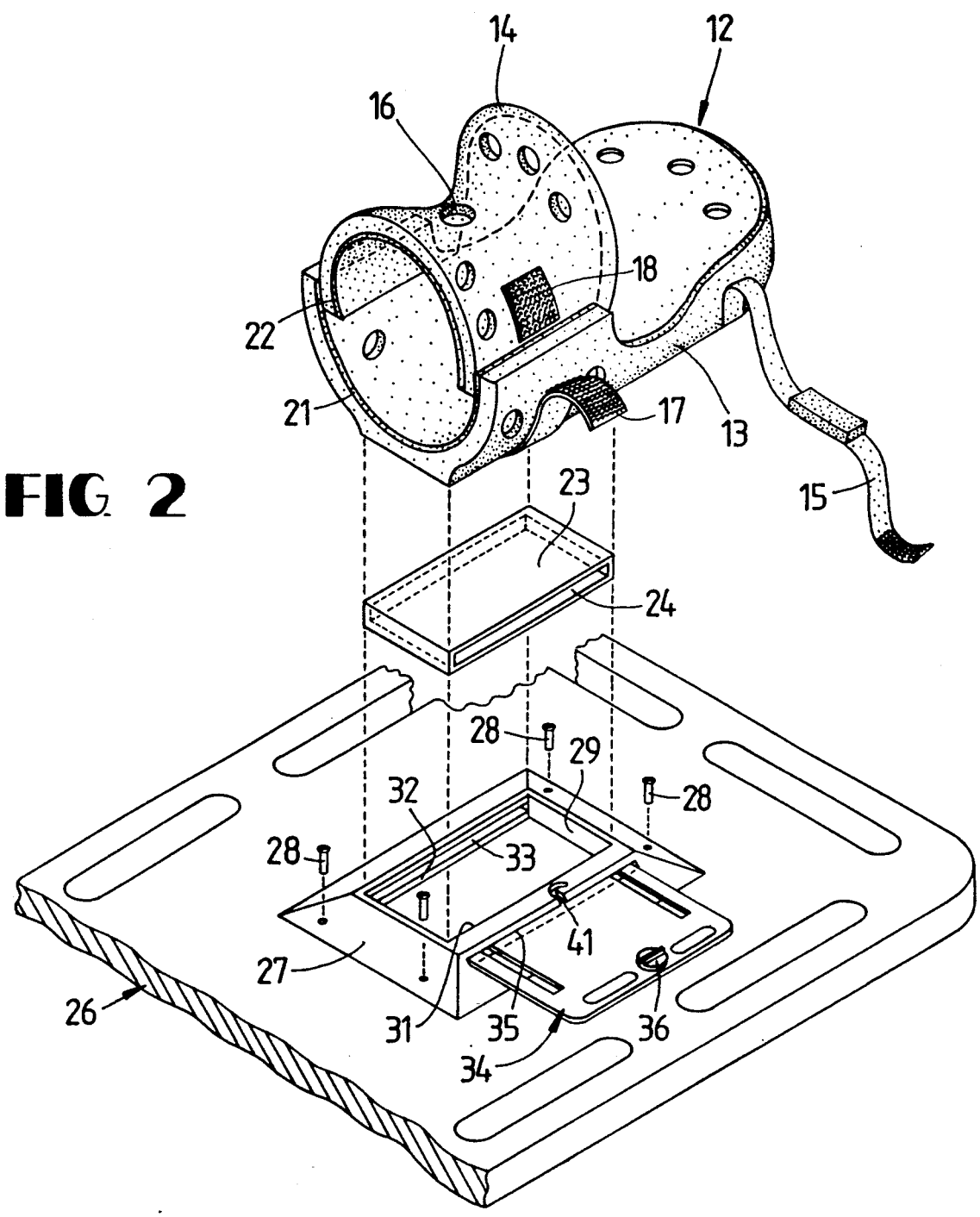
FIG. 2 is an exploded perspective view of the cervical collar, base locking frame and slide member.

A base 23 attaches to or is formed rearward of posterior member 13 as shown in FIG. 2. The base 23 is a rectangular structure having at least one rectangular opening 24 extending transversely therethrough when the base 23 and posterior member 13 are horizontally aligned with a backboard 26.

Figure 3:
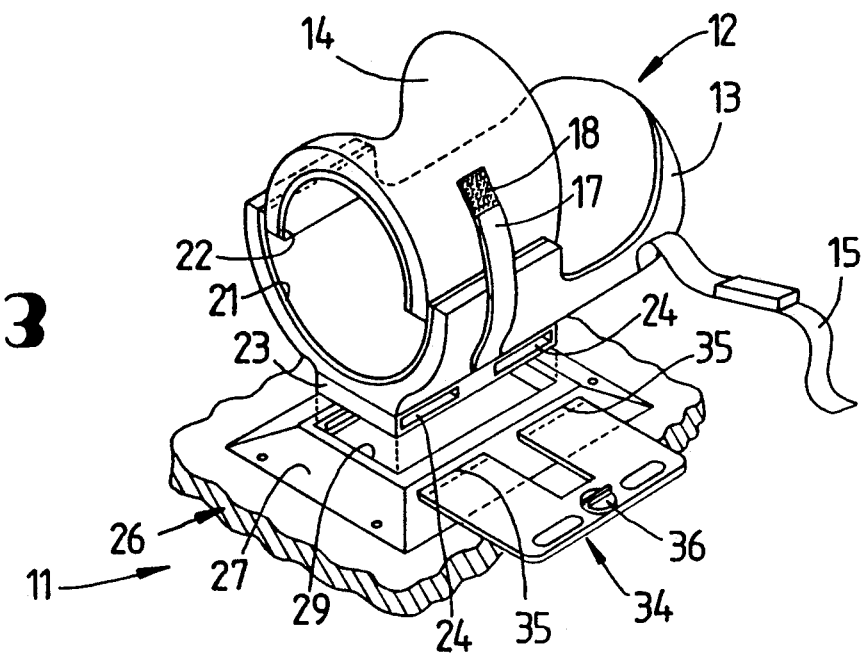
FIG. 3 is a perspective view of the present invention utilizing a U-shaped slide member.
Figure 4:
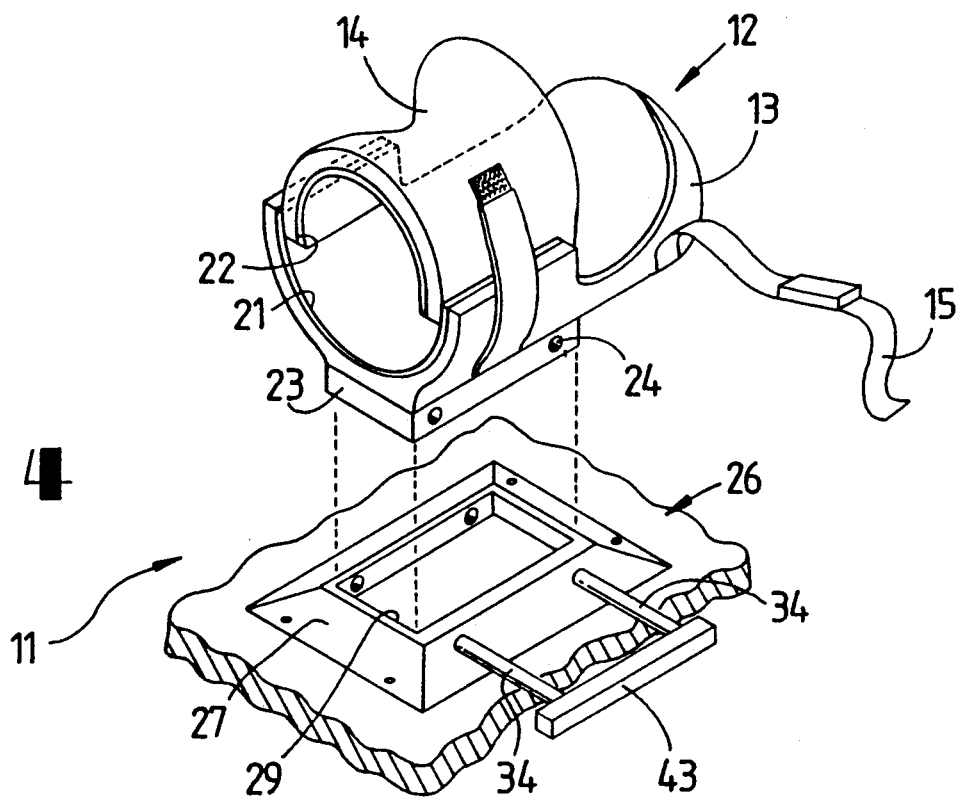
FIG. 4 is a perspective view of the present invention utilizing cylinder rod slide member.

In other embodiments, the base 23 has a pair of openings 24 in the form of rectangular slots as shown in FIG. 3. In FIG. 4 opening 24 is a pair of cylindrical holes extending through base 23.

As shown in FIG. 2 a frame 27 is mounted to a patient backboard 26 with fasteners 28. The frame 27 defines a rectangular inner recess 29. Recess 29 is of a dimension just slightly larger than base 23. The frame 27 is beveled downward and outward from defined inner recess 29. This beveled shape prevents frame 27 from snagging on a patient or related equipment when the patient is slid onto backboard 26 as shown in FIG. 5.

Figure 6:
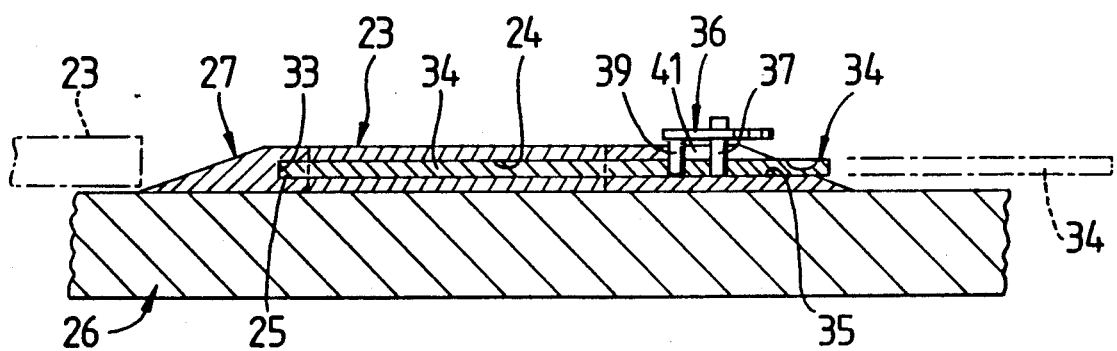
FIG. 6 is a cross-sectional view of the mounting plate taken along line 6—6 of FIG. 5.

At least one opening 35 extends transversely through a side 31 of frame 27. When mounted on board 26 as shown in FIGS. 2 and 6 opposing side 32 of frame 27 has a grooved channel 33 formed therein. A slidable securing member 34 is insertable within opening 35 for lateral sliding movement through side 31. The securing member 34 can slide within frame 27 such that the inserted end 25 engages channel 33.

Figure 5:
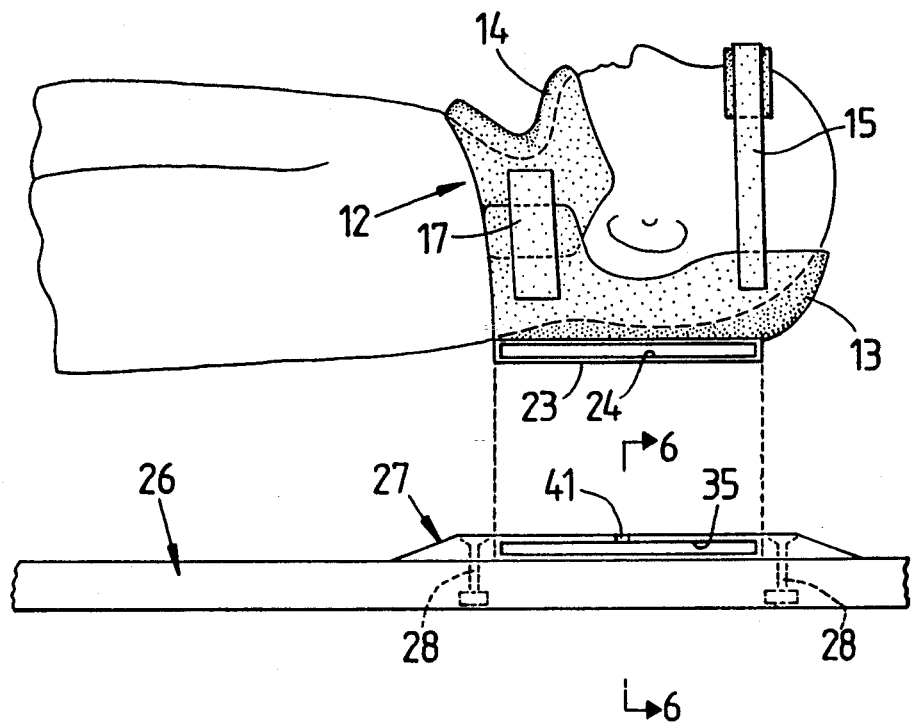
FIG. 5 is a side elevational view of the immobilizing device and attached base placed into locking frame.

When cervical collar 12 is in place around a supine patient's neck as shown in FIG. 5 the base 23 and aperture 24 are in a horizontal position. The base 23 is positional by EMTs within recess 29 allowing alignment of the base aperture 24 and frame aperture 35 of side 31 of frame 27. The slide member 34 may then be moved to extend through apertures 35 and 24 and base 23 to engage channel 33. Base 23 and attached collar 12 are thereby locked into position on backboard 26 to prevent movement of patient's head and cervical region. In FIG. 6 a cross-section view of backboard 26 and frame 27 shows the variable positions of slidable member 34.

Figure 9:
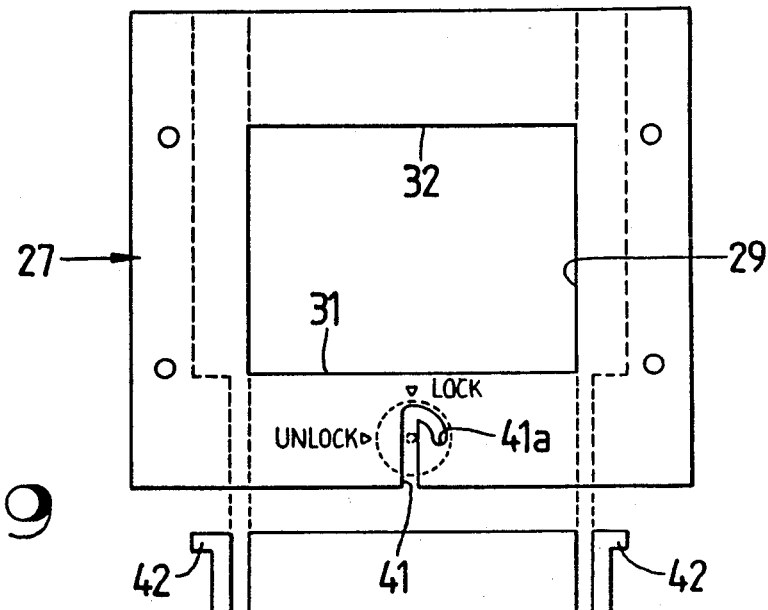
FIG. 9 is a plan view of the frame and plate including locking means.
Figure 10:
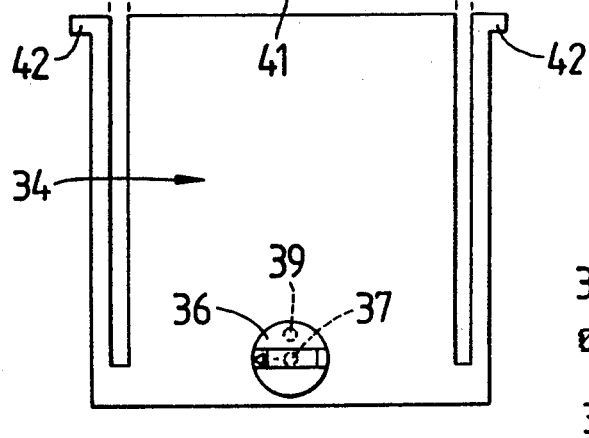
FIG. 10 is a side view of locking means.
Figure 11:
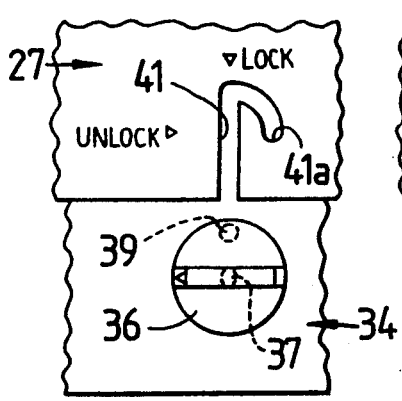
FIG. 11 is a top plan view of locking means as plate slide member is inserted.
Figure 12:
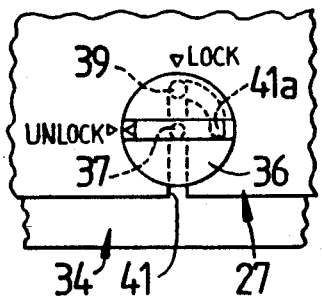
FIG. 12 is a top plan view of locking means inserted within frame.
Figure 13:
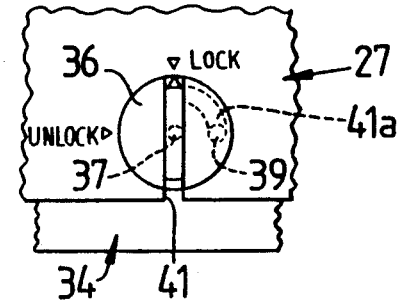
FIG. 13 is a top plan view of locking means in the locked position.

The slide member 34 can be locked in position relative to frame 27. FIG. 9 shows a plan view of the frame 27 and slide member 34. A disc knob 36 is mounted to surface of slide member 34 at an outer end. Disc knob 36 is rotatable about a vertical axis 37 and has a pin 39 mounted subjacent thereto as shown in FIG. 10. A hook shaped channel and groove 41 is cut into surface of side 31 of frame 27 in continuity with aperture 35. The disc knob 36 and pin 39 can be rotated into alignment, thereby allowing entry of pin 39 to channel 41 when slide member 34 is inserted as shown in FIG. 11. Once the slide member 34 is in place, FIGS. 12 and 13 show that disc knob 36 can be rotated to position pin 39 into the hook portion 41a of channel 41 locking the slide member 34 in place. FIG. 9 shows that flanges 42 extend outward from slide member 34 to prevent complete disengagement from frame 27. Flanges 42 may also extend vertically upward and downward to prevent disengagement.

The preferred embodiment shows sliding member 34 is a flat plate as shown in FIG. 2. Other embodiments include a slide member 34 formed in a U-shaped plate as shown in FIG. 3. In FIG. 4 the slide member 34 is a pair of cylindrical rods attached to a handle 43.

Figure 7:
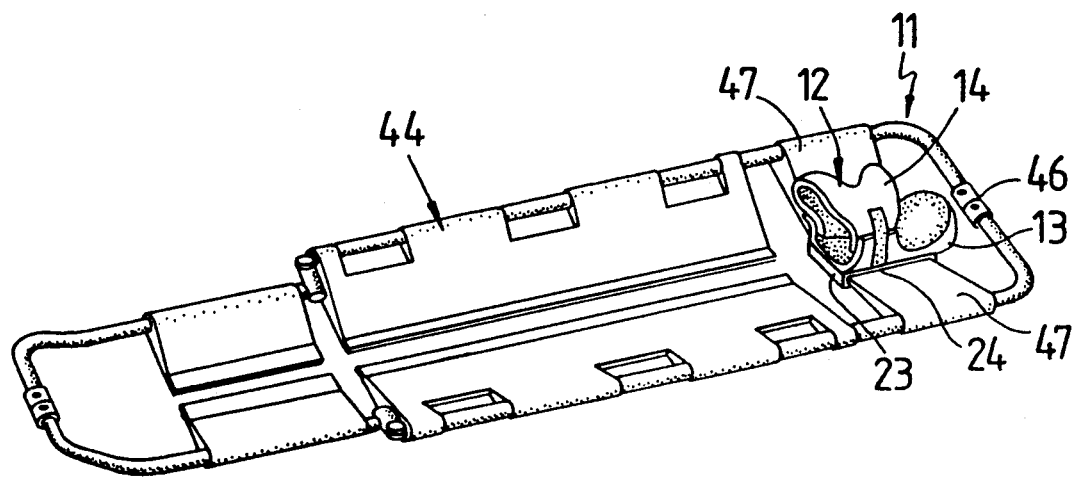
FIG. 7 is a perspective view of an immobilizing device and base attached to an orthopedic scoop stretcher.
Figure 8:
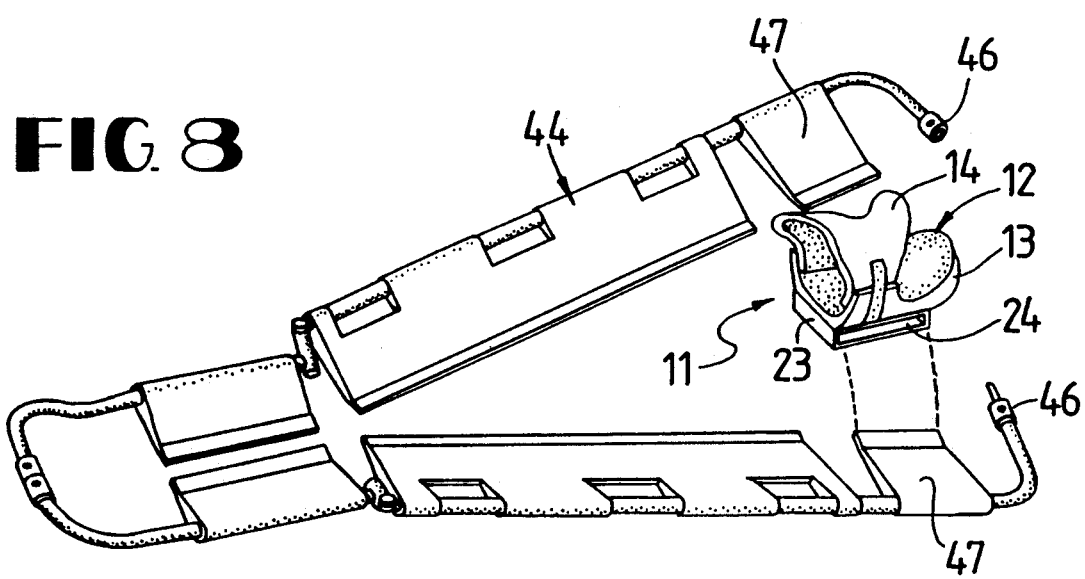
FIG. 8 is a perspective view of the orthopedic stretcher separated for attaching the immobilization collar and base.

The cervical collar 12 and attached base 23 may also be used on orthopedic scoop stretchers 44 as shown in FIGS. 7 and 8. The orthopedic scoop stretcher 44 disengages at connection 46 at top and bottom of stretcher frame 44 for positioning under a patient without lifting the patient. The base 23 and attached collar 12 can be positioned such that scoops 47 of stretcher 44 are inserted through aperture 24 as shown in FIG. 7. When stretcher 44 is reengaged at connection 46, collar 12 is secured in place to prevent movement and injury of patient.

It can be seen the present invention provides a cervical collar that is easily secured to a patient backboard. This invention provides a quick simple means to immobilize the head and cervical region of a patient for treatment and transport. While I have shown my invention in various forms, it will be obvious to those skilled in the art that it is not so limited but is susceptible of various changes and modifications without departing from the spirit thereof.

What I claim is:

1. In combination with a backboard, a cervical collar for immobilizing the head and neck of an injured person comprising:
   (a) a posterior member adapted for engagement behind the head and cervical region of a person, said member extending laterally therearound;
   (b) an anterior member adapted for engagement beneath the mandibular region, detachably secured to said posterior region to encircle said person's neck;
   (c) a base attached to said posterior member rearwardly thereof;
   (d) a patient backboard for supporting a horizontally disposed patient; and
   (e) a receiver attached to said patient backboard, said receiver having a recess for accepting said base, and a means for securing said base within said recess, said base having at least one opening extending transversely through said base for accepting said securing means when said base and said posterior member are in place on a patient.

2. A cervical collar as defined in claim 1 wherein said opening is a rectangular slot.

3. A cervical collar as defined in claim 1 wherein said base has a plurality of openings for accepting said securing means.

4. A cervical collar as defined in claim 3 wherein said plurality of openings includes a pair of cylindrical apertures.

5. A cervical collar as defined in claim 3 wherein said plurality of openings include a pair of rectangular slots.

6. A cervical collar as defined in claim 1 wherein said receiver is a rectangular frame defining an inner recess with a dimension slightly larger than said base for accepting said base, said frame having an opening extended therethrough for insertion of at least one slidable securing member for lateral movement relative said frame and said backboard, said slidable member positionable through said opening extending through said base for securing said base within said frame and a means for locking said slidable member in position.

7. A cervical collar as defined in claim 6 wherein said slidable securing member is a planar plate.

8. A cervical collar as defined in claim 6 wherein said slidable securing member is a pair of cylindrical rods.

9. A cervical collar as defined in claim 6 wherein said slidable securing member is a U-shaped planar plate.

10. A cervical collar as defined in claim 6 wherein said slidable securing member has formed thereon means for preventing disengagement of said receiving member from said base.

11. A cervical collar as defined in claim 6 wherein said locking means includes a hooked channel formed in said frame above and in continuity with said opening for inserting of said slidable securing member, said securing member having a disc mounted upon the upper surface relative said backboard thereon for rotation about a vertical axis, said disc having a pin protruding from lower surface of said disc for cooperative engagement with said channel to lock said securing member in place.

12. In combination with a patient backboard, a cervical collar for immobilizing the head and neck of an injured person comprising:
   (a) a posterior member adapted for engagement behind the head and cervical region of a person and extending laterally around;
   (b) an anterior member adapted for engagement beneath the mandibular region, detachably secured to said posterior region to encircle said injured person's neck;
   (c) a base attached to said posterior member rearwardly thereof, said base having at least one opening extending transversely therethrough; and
   (d) a receiver attached to said patient backboard, said receiver comprising a frame defining an inner recess with a dimension slightly larger than said base wherein said frame has an opening extending therethrough for insertion of at least one slidable securing member for lateral movement relative said frame and said backboard, said slidable member positionable through said opening in said base for securing said base within said frame.

13. A cervical collar as defined in claim 12 wherein said slidable securing member is a planar plate.

14. A cervical collar as defined in claim 12 wherein said slidable securing member is a pair of cylindrical rods.

15. A cervical collar as defined in claim 12 wherein said slidable securing member is a U-shaped planar plate.

16. A cervical collar as defined in claim 12 wherein said slidable securing member is flanged upwardly at an end of said plate proximal to said inner recess.

17. A cervical collar as defined in claim 12 wherein said receiver includes a hooked channel formed in one of said sides of said frame above and in continuity with said opening for inserting of said slidable securing member, said securing member having a disc mounted upon the upper surface relative said backboard thereon for rotation about a vertical axis, said disc having a pin protruding from lower surface of said disc for cooperative engagement with said channel to lock said securing member in place.

* * * * *